United States Patent [19]

Lacefield et al.

[11] Patent Number: 4,486,592
[45] Date of Patent: Dec. 4, 1984

[54] 9-CARBAMOYLFLUORENE DERIVATIVES

[75] Inventors: William B. Lacefield; Terry D. Lindstrom, both of Indianapolis, Ind.

[73] Assignee: Eli Lilly and Company, Indianapolis, Ind.

[21] Appl. No.: 543,200

[22] Filed: Oct. 19, 1983

[51] Int. Cl.³ .......................................... C07D 221/20
[52] U.S. Cl. ..................... 546/17; 564/147; 564/163; 564/164; 564/169; 564/180; 424/267; 424/324; 71/94; 71/118
[58] Field of Search .................. 546/17; 564/147, 164, 564/169, 180, 163

[56] References Cited

U.S. PATENT DOCUMENTS

| | | | |
|---|---|---|---|
| 4,197,313 | 4/1980 | Lacefield et al. | 424/304 |
| 4,277,495 | 7/1981 | Lacefield et al. | 424/309 |
| 4,282,170 | 8/1981 | Lavagnino et al. | 260/465 D |
| 4,382,093 | 5/1983 | Lacefield et al. | 424/324 |

Primary Examiner—Robert T. Bond
Attorney, Agent, or Firm—Charles W. Ashbrook; Arthur R. Whale

[57] ABSTRACT

9-Carbamoylfluorene derivatives are useful intermediates in a synthesis of 9-carbamoyl-9-(3-aminopropyl)-fluorene antiarrhythmic agents.

21 Claims, No Drawings

9-CARBAMOYLFLUORENE DERIVATIVES

BACKGROUND OF THE INVENTION

A group of 9-disubstituted fluorenes recently has been discovered to have potent antiarrhythmic activity; see U.S. Pat. Nos. 4,197,313 and 4,382,093. The 9-carbamoyl-9-aminoalkylfluorenes are among the most active compounds, and one compound within this group, namely 9-(3-isopropylaminopropyl)-9-carbamoylfluorene, is now known generically as indecainide. The reported syntheses of the 9-carbamoyl-9-aminoalkylfluorenes have included acid hydrolysis of a 9-cyano-9-aminoalkylfluorene, and more recently reductive alkylation of a 9-carbamoyl-9-cyanoalkylfluorene, see U.S. Pat. No. 4,282,170.

An object of the present invention is to provide a group of new compounds that are derivatives of 9-carbamoylfluorenes. Certain of the new compounds are useful as intermediates in a novel process for preparing 9-carbamoyl-9-aminoalkylfluorenes such as indecainide.

SUMMARY OF THE INVENTION

This invention provides compounds of the formula

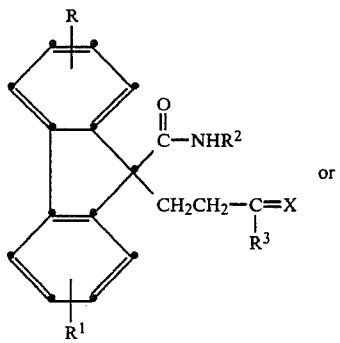

or

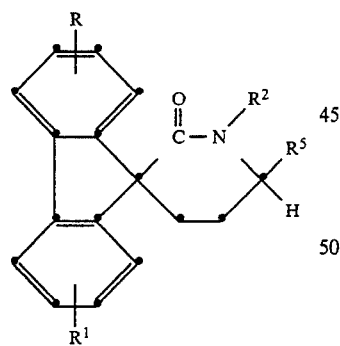

wherein

R and $R^1$ independently are hydrogen, $C_1$-$C_4$ alkyl, or halo;

$R^2$ is hydrogen or $C_1$-$C_6$ alkyl;

$R^3$ is hydrogen, hydroxy, or $C_1$-$C_4$ alkoxy;

X is O or N—$R^4$, where $R^4$ is $C_1$-$C_6$ alkyl, $CH_2C_2$-$C_5$ alkenyl or phenyl-$C_1$-$C_3$ alkyl, provided that $R^3$ is hydrogen when X is N—$R^4$; and $R^5$ is hydrogen or hydroxy.

A particularly preferred group of compounds which are useful as intermediates in the synthesis of antiarrhythmic agents are aldehydes of the formula

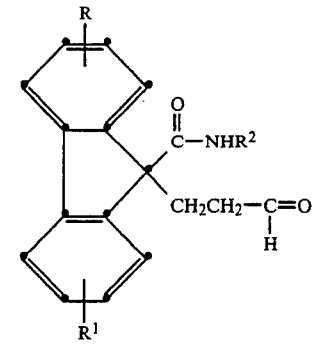

where R, $R^1$ and $R^2$ are as defined above. These compounds can exist in tautomeric equilibrium with another group of preferred compounds which are cyclic carbinols of the formula

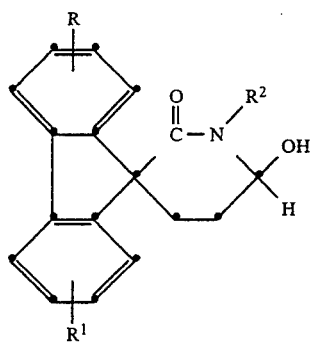

wherein R, $R^1$ and $R^2$ are as defined above. Reaction of the above aldehyde or a mixture of the aldehyde and the cyclic carbinol with a primary amine of the formula $H_2N$—$R^4$ provides another preferred group of compounds which are Schiff bases defined by the formula

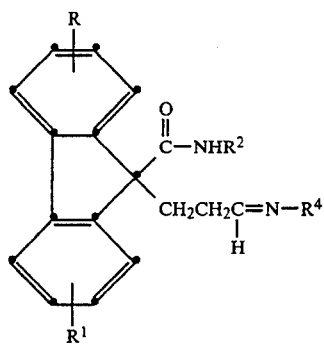

wherein R, $R^1$, $R^2$ and $R^4$ are as defined above. Reduction of these Schiff bases provides aminoalkylfluorene antiarrhythmic agents such as indecainide.

DETAILED DESCRIPTION OF THE INVENTION

In the above formulas, R and $R^1$ define substituents on the fluorene aromatic rings. The substituents can be hydrogen, $C_1$-$C_4$ alkyl such as methyl, ethyl, isopropyl, tert.-butyl and the like, or halo such as fluoro, chloro, bromo or iodo. Preferred compounds are those wherein R and $R^1$ both are hydrogen.

$R^2$ in the above formulas defines a substituent on the carbamoyl nitrogen atom and includes hydrogen and $C_1$-$C_6$ alkyl such as methyl, ethyl, n-propyl, n-butyl, 2-methylpentyl, iso-pentyl and the like. Preferred compounds of the invention are those wherein $R^2$ is hydrogen.

X in the above formulas is divalent oxygen or N—$R^4$, where $R^4$ is $C_1$-$C_6$ alkyl, $CH_2C_2$-$C_5$ alkenyl or phenyl-$C_1$-$C_3$ alkyl. The term "$C_1$-$C_6$ alkyl" carries its art recognized meaning and includes methyl, isopropyl, tert.-butyl, and 1,1-dimethylbutyl. A particularly preferred $R^4$ alkyl group is isopropyl. "$CH_2C_2$-$C_5$ Alkenyl" refers to groups such as allyl, 3-hexenyl, 4-pentenyl and the like. The term "phenyl-$C_1$-$C_3$ alkyl" includes benzyl, 2-phenylethyl and 3-phenylpropyl.

As noted above, a preferred group of compounds according to this invention are the aldehydes and cyclic carbinols which are tautomers of each other, compounds of the formulas

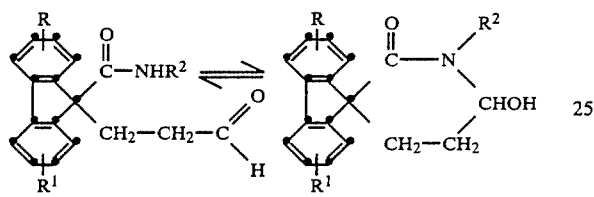

These compounds are readily prepared by reaction of a 9-carbamoylfluorene with acrolein with basic conditions according to the following scheme:

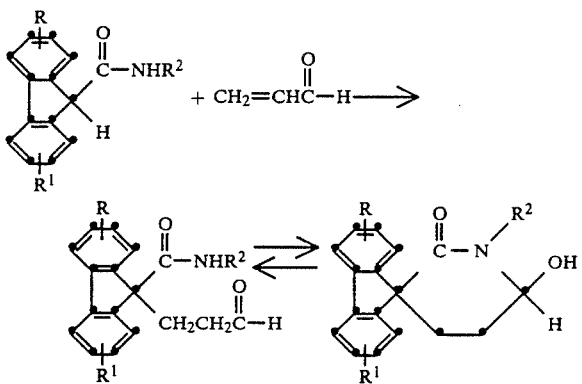

where R, $R^1$ and $R^2$ are as defined above. The reaction is carried out by combining the 9-carbamoylfluorene with acrolein in approximately equimolar quantities in the presence of a base. The particular base employed and the quantity are not critical, and an equimolar quantity or excess generally is used. Typical bases that can be employed include organic bases such as benzyltrimethyl ammonium hydroxide (Triton B), triethylamine, as well as alkali metal hydrides such as sodium hydride and potassium hydride. The reaction is preferably conducted in an organic solvent, and typical solvents include ethers such as diethyl ether and tetrahydrofuran, and aromatics such as benzene and toluene. The reaction typically is carried out at a temperature of about 0° to about 100° C., and at such temperature is usually complete within about one to about eight hours. The product of the reaction, a tautomeric mixture of an aldehyde and a cyclic carbinol, is readily isolated by removing the reaction solvent. The mixture can be crystallized from common solvents such as ethyl acetate and ether.

The tautomeric mixture of aldehyde and cyclic carbinol, compounds defined by the formulas

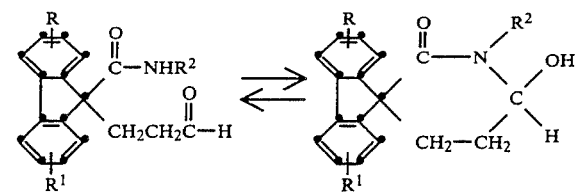

is useful as an intermediate in the synthesis of antiarrhythmic agents. For example, reaction of the tautomeric mixture with an equimolar quantity or excess of an amine of the formula $H_2N$—$R^4$ provides a Schiff base of the formula

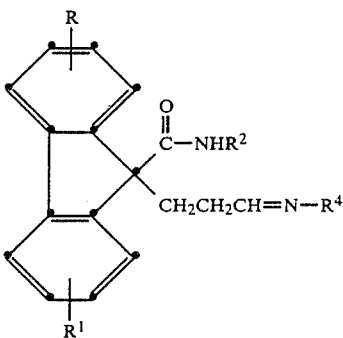

where R, $R^1$, $R^2$ and $R^4$ are as defined above. These Schiff base compounds are new compositions of matter and are provided as a further embodiment of this invention. Reaction of these Schiff bases with a reducing agent such as sodium borohydride or hydrogen and a catalyst such as palladium or platinum effects reduction of the carbon-nitrogen double bond to give the corresponding 9-carbamoyl-9-(3-aminoalkyl)fluorenes, which are useful as antiarrhythmic agents.

The reaction of an amine with the aldehydecarbinol tautomeric mixture can be carried out in a solvent such as acetonitrile or benzene, or if desired the amine can be employed in sufficient quantity to serve as reactant and solvent. The pH of the reaction mixture is ideally maintained at about 6 to about 10, and added base can be employed for this purpose if desired. The reaction generally is conducted at a temperature of about −20° to about 100° C., and usually is substantially complete after about two to about twentyfour hours. The Schiff base that is formed can be isolated by employing routine procedures, but preferably is not isolated but is simply subjected to reduction so as to produce the desired 9-carbamoyl-9-(3-aminopropyl)-fluorene antiarrhythmic agent.

Another preferred group of compounds provided by this invention are those of the formula

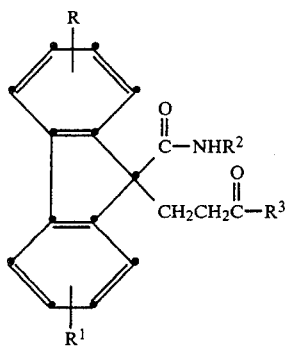

wherein R, R$^1$ and R$^2$ are as defined above and R$^3$ is hydroxy or C$_1$–C$_4$ alkoxy. These compounds are prepared by reaction of a 9-carbamoylfluorene with an alkyl acrylate of the formula

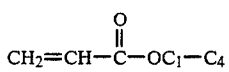

in the presence of a base such as Triton B or the like. The reaction is generally carried out in an unreactive organic solvent such as diethyl ether or tetrahydrofuran, and is generally complete after about three hours when conducted at a temperature of about 0 to about 100° C. The product, a 9-carbamoyl-9-(2-alkoxycarbonylethyl)fluorene, can be isolated by removal of the reaction solvent and crystallization from common solvents such as ethanol and petroleum ether. Acid or base hydrolysis of the 9-(2-alkoxycarbonylethyl)-fluorene derivative under routine conditions affords the corresponding acid, a 9-carbamoyl-9-(2-hydroxycarbonylethyl)fluorene. Pyrolysis of the 9-carbamoyl-9-(2-alkoxycarbonylethyl or 2-hydroxycarbonylethyl)-fluorene effects cyclization to provide a spiro fluorene derivative of the formula

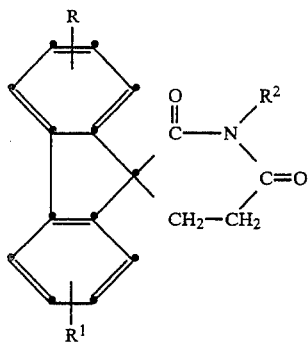

wherein R, R$^1$ and R$^2$ are as defined above.

Another group of spiro fluorene derivatives defined by the formula

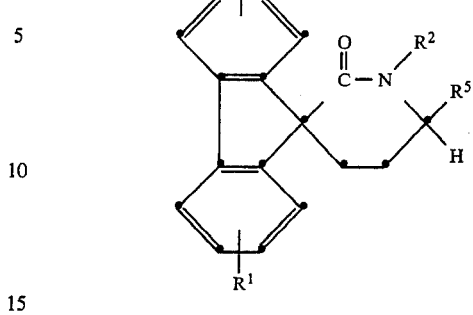

wherein R, R$^1$ and R$^2$ are as defined above and R$^5$ is hydrogen are prepared by pyrolysis of a 9-alkoxycarbonyl-9-(3-aminopropyl)fluorene, generally in the presence of an acid such as 1N hydrochloric acid or the like.

The following Table I presents classes of compounds and specific compounds provided in an effort to more fully illustrate the invention.

TABLE I

A. Compounds of the formulas

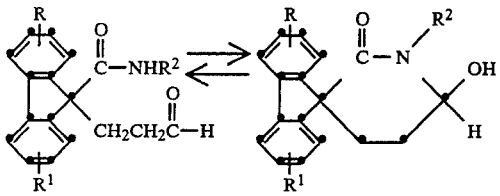

1. R$^2$ is hydrogen
   A1.a. R and R$^1$ both are hydrogen
   A1.b. R is hydrogen and R$^1$ is 2-methyl
   A1.c. R is 4-ethyl and R$^1$ is 6-chloro
   A1.d. R is 2-fluoro and R$^1$ is 7-bromo
2. R$^2$ is methyl
   A2.a. R and R$^1$ both are hydrogen
   A2.b. R is hydrogen and R$^1$ is 3-isopropyl
   A2.c. R is 3-methyl and R$^1$ is 6-ethyl
3. R$^2$ is n-hexyl
   A3.a. R and R$^1$ both are hydrogen
   A3.b. R is 2-chloro and R$^1$ is 6-chloro Compounds of the formula

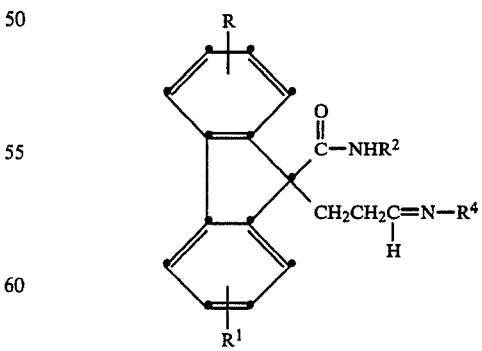

1. R$^2$ is hydrogen,
   a. R$^4$ is methyl
   B1.a1 R and R$^1$ both are hydrogen
   B1.a2 R is 2-ethyl and R$^1$ is hydrogen
   B1.a3 R is 4-fluoro and R$^1$ is 5-n-butyl b. $R^4$ is isopropyl
B1.b1 R and $R^1$ both are hydrogen
B1.b2 R is 1-fluoro and $R^1$ is hydrogen
B1.b3 R is 2-methyl and $R^1$ is 6-iodo
  c. $R^4$ is benzyl
B1.c1 R and $R^1$ both are hydrogen
B1.c2 R is 4-ethyl and $R^1$ is 5-fluoro
B1.c3 R is 2-fluoro and $R^1$ is 7-fluoro
  d. $R^4$ is allyl
B1.d1 R and $R^1$ both are hydrogen
 2. $R^2$ is ethyl
  a. $R^4$ is 2-phenylethyl
B2.a1 R and $R^1$ both are hydrogen
B2.a2 R is 2-fluoro and $R^1$ is hydrogen
B2.a3 R is 3-methyl and $R^1$ is 6-methyl
  b. $R^4$ is sec.-butyl
B2.b1 R and $R^1$ both are hydrogen
B2.b2 R is 2-fluoro and $R^1$ is hydrogen
  c. $R^4$ is 3-hexenyl
B2.b1 R and $R^1$ both are hydrogen
B2.b2 R is 3-fluoro and $R^1$ is 6-fluoro C. Compounds of the formula

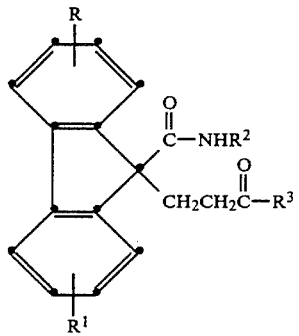

1. $R^2$ is hydrogen
  a. $R^3$ is methoxy
C1.a1 R and $R^1$ both are hydrogen
C1.a2 R is hydrogen and $R^1$ is 2-fluoro
C1.a3 R is 3-bromo and $R^1$ is hydrogen
C1.a4 R is 2-methyl and $R^1$ is 6-iodo
  b. $R^3$ is tert.-butoxy
C1.b1 R is 4-chloro and $R^1$ is 5-bromo
C1.b2 R is 2-methyl and $R^1$ is 6-n-butyl
  c. $R^3$ is hydroxy
C1.c1 R is 3-fluoro and $R^1$ is 6-methyl
 2. $R^2$ is isobutyl
  a. $R^3$ is ethoxy
C2.a1 R and $R^1$ both are hydrogen
C2.a2 R is 1-fluoro and $R^1$ is hydrogen
  b. $R^3$ is hydroxy
C2.b1 R and $R^1$ both are hydrogen D. Compounds of the formula

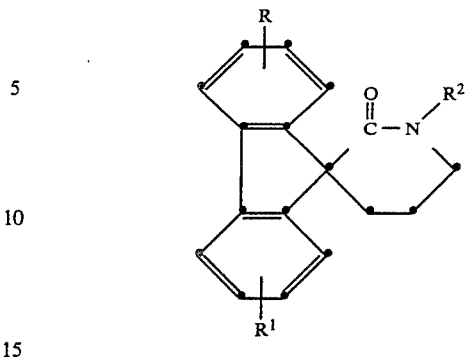

1. $R^2$ is hydrogen
D1.a R and $R^1$ both are hydrogen
D1.b R is 2-fluoro and $R^1$ is 6-iodo
D1.c R is 3-isopropyl and $R^1$ is 7-bromo
 2. $R^2$ is n-hexyl
D2.a R and $R^1$ both are hydrogen
D2.b R is 2-fluoro and $R^1$ is 6-n-butyl
D2.c R is 4-ethyl and $R^1$ is 8-methyl The following detailed examples further illustrate the synthesis of compounds provided by this invention.

EXAMPLE 1

6'-Hydroxyspiro(9H-fluorene-9,3'-piperidine)-2'-one

A solution of 10.0 g (48 mM) of 9-carbamoylfluorene in 100 ml of tetrahydrofuran was heated to 45° C. and stirred under a nitrogen blanket while 2 ml of N-benzyl-trimethyl ammonium hydroxide (Triton B) were added in one portion. The reaction mixture was stirred for fifteen minutes at 45° C., and then 2.8 g (50 mM) of acrolein were added dropwise over ten minutes. The reaction mixture was heated at reflux for three hours following the addition. The reaction mixture was cooled to room temperature and concentrated to an oil by evaporation of the solvent under reduced pressure. The oil was dissolved in 100 ml of ethyl acetate and washed with water. The organic layer was dried and the solvent was removed by evaporation to provide a solid. The solid was crystallized from ethyl acetate and petroleum ether to give 4.0 g of solid product. The product was purified further by high pressure liquid chromatography over silica gel, eluting with chloroform containing 5% (v/v) methanol. The appropriate fractions were combined and concentrated to dryness to afford 500 mg of 6'-hydroxyspiro(9H-fluorene-9,3'-piperidine)-2'-one melting at 210°–212° C.

Analysis calculated for $C_{17}H_{15}NO_2$ (after drying at 120° C.):
Theory: 76.96; H, 5.70; N, 5.28; O, 12.06. Found: 76.66; H, 5.99; N, 5.21; O, 12.27.
Mass Spec. M+ Theory 265, Found 265.
NMR (DMSOd$_6$): δ1.6–2.5 (m, 4H); 5.32 (broad s, 1H): 6.12 (d, 1H); 7.3–8.1 (m, 8H); 8.32 (d, 1H).
IR (KBr): 1642 cm$^{-1}$ (amide)

EXAMPLE 2

Following the general procedure of Example 1, 20.9 g (0.1 mole) of 9-carbamoylfluorene were added to 300 ml of tetrahydrofuran. The solution was heated to 50° C. and stirred while 6 ml of benzyltrimethylammonium hydroxide were added in one portion. After stirring the reaction mixture at 50° C. for thirty minutes, 6.2 g (0.11 mole) of acrolein were added and the mixture was then heated at reflux for four hours. The reaction mixture was cooled to 25° C. and the solvent was removed by evaporation under reduced pressure to provide 29.9 g of 6′-hydroxyspiro(9H-fluorene-9,3′-piperidine)-2′-one and its tautomeric isomer 9-carbamoyl-9-(3-oxopropyl)-fluorene. m.p. 199°–201° C.

Analysis (after drying at 120° C. for one minute) Calculated for $C_{17}H_{15}NO_2$ Theory: C, 76.96; H, 5.70; N, 5.28. Found: C, 76.71; H, 5.88; N, 5.23.

Mass Spec. M+ Theory 265; Found 265.

NMR ($CDCl_3+DMSOd_6$): δ1.7–2.6 (m, 4H); 5.3 (broad s, 1H); 5.9 (d, 1H); 7.2–7.9 (m, 9H).

IR (KBr): 1639 cm$^{-1}$ (amide)

The general procedure of Example 1 was again followed when a solution of N-benzyltrimethylammonium hydroxide (Triton B) which is a 40% methanolic solution (3.5 ml) in acetonitrile (10 ml) was added dropwise over 0.25 hour to a suspension of 9-carbamoylfluorene (20.9 g) in acetonitrile (100 ml) keeping the temperature below 25° C. The reaction mixture was stirred at room temperature for 2 hours. Water (300 ml) was then added slowly over 1 hour and the crystallized product was isolated by filtration, washed with water and dried in vacuo overnight at 50° C. to give 89% yield of 6′-hydroxyspiro(9H-fluorene-9,3′-piperidine)-2′-one melting at 201°–205° C. (decomp). The product was identical spectroscopically to that prepared in Example 1.

EXAMPLE 3

9-Carbamoyl-9-(3-isopropyliminopropyl)fluorene

A mixture of 5.9 g (0.1 mole) of isopropylamine and 2.5 g (0.009 mole) of the tautomeric mixture from Example 2 was stirred at 25° C. under a nitrogen blanket for sixteen hours. Excess isopropylamine was removed by evaporation under reduced pressure to provide, following crystallization from ethylacetate and petroleum ether, 0.7 g (25% yield) of a solid identified as 9-carbamoyl-9-(3-isopropyliminopropyl)fluorene. m.p. 149°–155° C.

M+ Theory 306; Found 306.

NMR ($CDCl_3$): δ1.0 (two s, 6H); 1.62 (m, 2H); 2.65 (m, 2H); 3.06 (m, 1H); 5.05 (broad s, 2H, signal removed with $D_2O$ shake); 7.28–7.79 (m, 9H).

EXAMPLE 4

Preparation of 9-carbamoyl-9-(3-isopropylaminopropyl)fluorene hydrochloride

9-Carbamoyl-9-(3-isopropyliminopropyl)fluorene, prepared as described in Example 3, was dissolved in 200 ml of ethanol containing 3.0 g of 5% palladium on carbon. The reaction mixture was shaken in an hydrogen atmosphere at 25° C. for six hours. The actual hydrogen uptake was 19.5 lbs; theoretical uptake was 19.7 lbs. The reaction mixture was filtered to remove the hydrogenation catalyst and the filtrate was concentrated to dryness by evaporation under reduced pressure. The solid that was formed was dissolved in 100 ml of diethyl ether containing 100 ml of ethyl acetate. The product was extracted into 6N hydrochloric acid and the acid extracts were combined, cooled to 10° C. and made alkaline to pH 10.0 by addition of 10% (w/v) aqueous sodium hydroxide. The alkaline solution was extracted several times with fresh diethyl ether, and the ethereal extracts were combined, washed with water, dried, and then saturated with gaseous hydrogen chloride. The precipitate which formed was collected by filtration and recrystallized from ethanol and diethyl ether to give 2.1 g of 9-carbamoyl-9-(3-isopropylaminopropyl)fluorene hydrochloride (indecainide hydrochloride). m.p. 206°–207.5° C.

Analysis calculated for $C_{20}H_{25}ClN_2O$ Theory: C, 69.65; H, 7.31; N, 8.12. Found: C, 69.55; H, 7.18; N, 7.99.

IR (KBr): 1680, 1665 cm$^{-1}$

NMR ($DMSOd_6$): δ1.08 (s, 3H); 1.19 (s, 3H); 2.2–2.9 (m, 6H); 6.28 (s, 1H); 7.0 (s, 1H); 7.3–8.1 (m, 9H); 8.8 (broad s, 2H).

Titration (66% v/v N,N-dimethylformamide-water) $pK_a=10.2$

The general procedure described above was followed when 6′-Hydroxyspiro-(9H-fluorene-9,3′-piperidine)-2′-one (2.7 g) was dissolved in isopropylamine (350 ml) and 10% palladium on charcoal (0.3 g) was added and the vessel pressurized to 90 p.s.i. with hydrogen. The reaction mixture was then heated at 40° for 16 hours and then allowed to cool to room temperature. The catalyst was removed by filtration and the isopropylamine evaporated under reduced pressure. The resulting residue was dissolved in dichloromethane (20 ml) washed with water (2×50 ml), dried with anhydrous sodium sulphate and evaporated to dryness under reduced pressure. The residue was triturated with hexane to give 9-carbamoyl-9-(3-isopropylaminopropyl)fluorene crystals.

EXAMPLE 5

9-Carbamoyl-9-(3-isopropylaminopropyl)fluorene

The pH of a cold (10° C.) solution of 12.0 ml of isopropylamine in 500 ml of acetonitrile was adjusted to 8.0 by addition of gaseous hydrogen chloride. While the reaction mixture was stirred there were added sequentially 2.0 g of sodium cyanoborohydride and 5.4 g of 6′-hydroxyspiro(9H-fluorene-9,3′-piperidine)-2′-one (the cyclic carbinol and its tautomer prepared as described in Examples 1 and 2). The reaction mixture was heated at reflux for six hours, cooled to 25° C. and then diluted by addition of 100 ml of 1N hydrochloric acid. The organic solvent was removed by evaporation under reduced pressure. The aqueous solution was washed several times with dichloromethane, made alkaline by addition of ammonium hydroxide, and the product was extracted into fresh dichloromethane. The organic extracts were combined, washed with water, dried and concentrated to dryness to give 70% yield of 9-carbamoyl-9-(3-isopropylaminopropyl)fluorene, the identity of which was confirmed by thin layer chromatographic comparison with an authenic sample (silica gel, ethyl acetate:methanol, 80:20 v/v).

The general procedure thus described was repeated when a solution of isopropylamine (45.0 ml) in acetonitrile (250 ml) was cooled to 10° C. and hydrogen chloride gas introduced into the solution keeping the temperature below 15° to pH 8.5±0.3. The resultant slurry was allowed to warm to room temperature and sodium cyanoborohydride (12.0 g) added in one portion and the pH readjusted to 8.5 if necessary. 6′-Hydroxyspiro-(9H-fluorene-9,3′-piperidine)-2′-one (30.0 g) was then added and the reaction mixture heated to reflux for 2 hours. The mixture was allowed to cool to room temperaure and dilute hydrochloric acid added to pH 1–2 to destroy any excess cyanoborohydride. The acetonitrile was removed under reduced pressure and the residue basified with sodium hydroxide solution (pH 11) and extracted with dichloromethane (3×100 ml) and the combined organic layers washed with sodium hydroxide solution, dried with anhydrous sodium sulphate and evaporated to give the crystalline free amine.

This amine was dissolved in acetone (120 ml) and cooled to 15° C. Dry hydrogen chloride gas was passed through the solution until a pH of 7 was obatined. The resultant mixture was cooled slowly to −30°, and the produce isolated by filtration, washed with cold acetone, and dried in vacuo at 40° overnight to give 9-carbamoyl-9-(3-isopropylaminopropyl)fluorene hydrochloride.

EXAMPLE 6

9-Carbamoyl-9-(2-tert.-butoxycarbonylethyl)fluorene

A solution of 35.5 g (169 mM) of 9-carbamoylfluorene in 1000 ml of tetrahydrofuran containing 10 ml of Triton B was heated at 45° C. for fifteen minutes. Twenty-five grams (176 mM) of tert.-butylacrylate were added in one portion to the reaction mixture, and the mixture was heated at reflux for three hours. The reaction mixture was filtered and the filtrate was concentrated to dryness to give 40.0 g of an oil. The oil was dissolved in 500 ml of ethyl acetate and washed with water, dried, and the solvent was removed by evaporation under reduced pressure to give a white solid. The solid was crystallized twice from ethyl acetate and petroleum ether to give 16.75 g of 9-carbamoyl-9-(2-tery.-butoxycarbonylethyl)fluorene. m.p. 157°–159° C.

Analysis calculated for $C_{21}H_{23}NO_3$ Theory: C, 74.75; H, 6.87; N, 4.15. Found: C, 75.03; H, 6.74; N, 3.93.

NMR (CDCl$_3$): δ 1.3 (s, 9H); 1.3–1.7 (m, 2H); 2.5–2.9 (m, 2H); 5.0–5.7 (broad d, 2H); 7.3–7.9 (m, 8H).

IR (KBr): 1695 cm$^{-1}$ (amide carbonyl) 1740 cm$^{-1}$ (ester carbonyl).

EXAMPLE 7

9-Carbamoyl-9-(2-hydroxycarbonylethyl)fluorene

A solution of 1.0 g (2 mM) of 9-carbamoyl-9-(2-tert.-butoxycarbonylethyl)fluorene (from Example 6) in 3 ml of trifluoroacetic acid was stirred at 25° C. for four minutes. The reaction mixture was concentrated to dryness by evaporation under reduced pressure to provide an oil. The oil was triturated with diethyl ether and dried to give 670 mg of 9-carbamoyl-9-(2-hydroxycarbonylethyl)fluorene. m.p. 191°–192° C.

Analysic calculated for $C_{17}H_{15}NO_3$; Theory: C, 72,58; H, 5.37; N, 4.98. Found: C, 72.41; H, 5.27; N, 4.84.

NMR (DMSOd$_6$): δ 1.35–1.72 (m, 2H); 2.4–2.8 (m, 2H); 3.1–4.1 (broad s, 1H); 6.22 and 7.02 (two 5, 2H); 7.4–8.2 (m, 8H).

IR (KBr): 1660 cm$^{-1}$ (carboxylic acid); 1710 cm$^{-1}$ (carboxamide).

EXAMPLE 8

Spiro(9H-fluorene-9,3'-piperidine)-2',6'-dione

One and one-half grams (4 mM) of 9-carbamoyl-9-(2tert.-butoxycarbonylethyl)fluorene (from Example 6) were heated at 180° C. for twenty minutes and at 160° C. for an additional one hour. The mixture was cooled and triturated with a mixture of 25 ml of ethyl acetate and 75 ml of toluene. The product was then purified by high pressure liquid chromatography over a silica gel support, eluting with a gradient of 10 to 25% (v/v) ethyl acetate in toluene. Fractions shown to contain one component were combined and concentrated to dryness to give, following crystallization from ethyl acetate and petroleum ether, spiro(9H-fluorene-9,3'-piperidine)-2',6'-dione melting at 224°–225° C.

Analysis calculated for $C_{17}H_{13}NO_2$ Theory: C, 77.55; H, 4.98; N, 5.32. Found: C, 77.56; H, 5.12; N, 5.11.

NMR (CDCl$_3$+DMSOd$_6$): δ 2.25 (t, 2H); 3.0 (t, 2H); 7.4–8.0 (m, 8H); 8.1–9.5 (broad s, 1H).

Mass Spec. M+ 268.

EXAMPLE 9

Spiro(9H-fluorene-9,3'-piperidine)-2'-one

A solution of 5.0 g (18.8 mM) of 9-carbamoyl-9-(3-aminopropyl)fluorene (prepared as described in U.S. Pat. No. 4,282,170) in 50 ml of methanol saturated with hydrogen chloride was heated at reflux for sixteen hours. The reaction mixture was cooled and concentrated to dryness to give a solid. The solid was dissolved in 1N hydrochloric acid and the solution was heated to 100° C. for five minutes. The acidic mixture was diluted by addition of 50% aqueous sodium hydroxide to pH 10. The aqueous alkaline solution was extracted several times with chloroform, and the extracts were combined, washed with water and with brine and dried. Removal of the solvent by evaporation under reduced pressure provided a solid that was crystallized from dichloromethane and petroleum ether to afford 3.4 g of spiro(9H-fluorene-9,3'-piperidine)-2'-one. m.p. >250° C.

As pointed out above and demonstrated in the foregoing Examples, the cyclic carbinol and aldehyde tautomers are preferred compounds since they are readily reacted with a primary amine to provide the Schiff bases of the invention, which are subsequently reduced to provide 9-carbamoyl-9-(3-aminopropyl)fluorene anti-arrhythmic agents. Other compounds of the invention have biological properties which render them useful. For example, the carboxylic acid derivatives of the formula

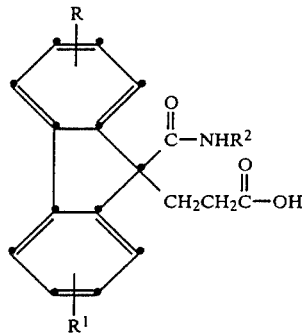

have been found to display useful pre- and post-emergence herbicidal activity against a variety of weed species commonly occurring in areas utilized for growing desired crops such as the cereal grains, corn, soybeans and the like. The selective herbicidal activity of the compounds has been analyzed in a broad spectrum greenhouse test carried out by filing square plastic pots with a sterilized sandy loam soil and planting seeds of tomato, large crabgrass and pigweed. Each pot was fertilized with a 23-21-17 fertilizer four days before treatment with test compound.

The test compounds were formulated for application by dissolving each compound in a solution comprising 100 ml of acetone and 100 ml of ethanol plus 1.174 g of Tomixul R and 0.783 g of Toximul S. (Toximul R and Toximul S are proprietary blends of anionic and nonionic surfactants manufactured by Stephen Chemical Company, Northfield, IL). Each test compound was dissolved in the diluent at the rate of 20 mg per 2 ml of solvent, and then the solution was diluted to 8 ml with deionized water. The formulated compounds were applied to the planted pots at an effective rate of 15 pounds per acre (16.816 kg per hectare).

Test compounds were applied postemergence to some planted pots and preemergence to others. The postemergence applications were made by spraying the solution containing the test compound over the emerged plants about twelve days after the seeds were planted. Preemergence applications were sprayed on the soil one day after the seeds were planted.

Following application of the test compounds, the pots were placed in a greenhouse and watered as necessary. Observations were conducted about 10-13 days following application of the test compounds, and untreated control plants were used as standards in each observation. The degree of herbicidal activity of the test compounds was determined by rating the treated plants on a scale of 1-5. On this scale, "1" indicates no plant injury; "2" is slight injury; "3" is moderate plant injury; "4" is severe injury and "5" is death of the plant or no seedling emergence. The type of plant injury sustained by the plants was tabulated using the following code letters:

A = Abscission of leaves
B = burned
C = chloris
D = death
E = epinasty
S = stunting Table II below presents the herbicidal activity of a representative compound of the invention when evaluated according to the foregoing method.

TABLE II

| Compound of Example No. | Preemergence | | | Postemergence | | |
|---|---|---|---|---|---|---|
| | Tomato | Large Crabgrass | Pigweed | Tomato | Large Crabgrass | Pigweed |
| 7 | 1 | 1 | 5D | 1 | 2S | 2S |

Compounds having such herbicidal activity can be admixed with conventional carriers and applied to soil at the rate of about 1 to about 25 lb/A for the control of growth of unwanted vegetation such as pigweed and the like.

The carboxylic acid esters of the invention, compounds of the above formula wherein X is O and $R^3$ is $C_1$-$C_4$ alkoxy, are useful as anticoccidials, antibacterials, and have influence on blood platelet aggregation. For example, 9-carbamoyl-9-(2-tert.-butoxycarbonylethyl)fluorene, the compound of Example 6, was active in vitro at 10 mcg/disc against *mycoplasma gallisepticum*, and was active at 100 mcg/disc against *Lactobacillus* sp. and *Escherichia coli*. When evaluated in a standard in vitro assay for anticoccidial activity, the compound effectively suppressed development of *Eimeria tenella* parasites at concentration levels of 10, 5 and 1 parts per million (ppm).

The spiro fluorenes wherein $R^5$ in the above formula is hydroxy are similar to the carboxylic acid esters in that they display anticoccidial activity. The compound of Example 9 was active at 10 ppm against *Eimeria tenella* when evaluated in an in vitro tissue culture assay. These spiro fluorene derivatives also have useful diuretic activity, and such activity was confirmed for the compound of Example 9 at an oral dose in rats of 10 mg/kg.

The compounds of the invention having anticoccidial activity can be formulated with conventional diluents and carriers such as rice hulls and soybean meal and administered to poultry at the rate of about 1 to about 50 mg/kg for the control and prevention of coccidiosis.

We claim:

1. A compound having the formula

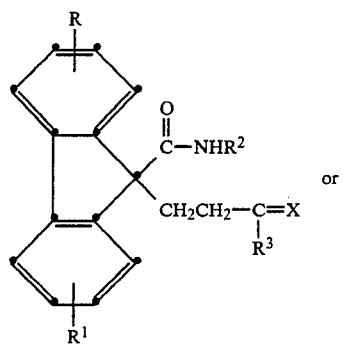

or

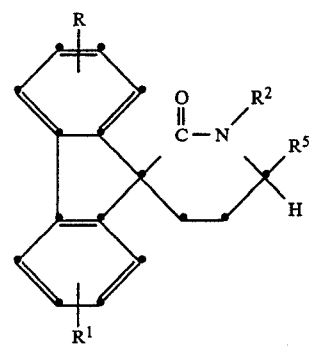

wherein
R and $R^1$ independently are hydrogen, $C_1$-$C_4$ alkyl, or halo;
$R^2$ is hydrogen or $C_1$-$C_6$ alkyl;
$R^3$ is hydrogen, hydroxy, or $C_1$-$C_4$ alkoxy;
X is O or N-$R^4$, where
$R^4$ is $C_1$-$C_6$ alkyl, $CH_2C_2$-$C_5$ alkenyl or phenyl-$C_1$-$C_3$ alkyl, provided that $R^3$ is hydrogen when X is N-$R^4$; and
$R^5$ is hydrogen or hydroxy.

2. A compound of claim 1 having the formula

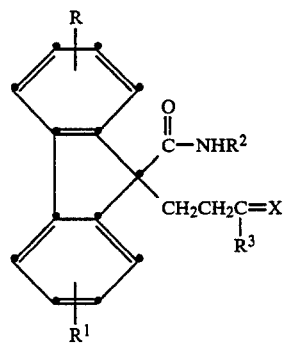

wherein $R^2$ is hydrogen.

3. The compound of claim 2 wherein X is O and $R^3$ is hydrogen.

4. The compound of claim 3 wherein R and $R^1$ both are hydrogen.

5. The compound of claim 2 wherein X is O and $R^3$ is $C_1$–$C_4$ alkoxy.

6. The compound of claim 5 wherein R and $R^1$ both are hydrogen.

7. The compound of claim 6 wherein $R^3$ is tert.-butoxy.

8. The compound of claim 2 wherein X is O and $R^3$ is hydroxy.

9. The compound of claim 8 wherein R and $R^1$ both are hydrogen.

10. The compound of claim 2 wherein X is N–$R^4$ and $R^3$ is hydrogen.

11. The compound of claim 10 wherein $R^4$ is $C_1$–$C_6$ alkyl.

12. The compound of claim 11 wherein $R^4$ is isopropyl.

13. The compound of claim 12 wherein R and $R^1$ both are hydrogen.

14. A compound of claim 1 having the formula

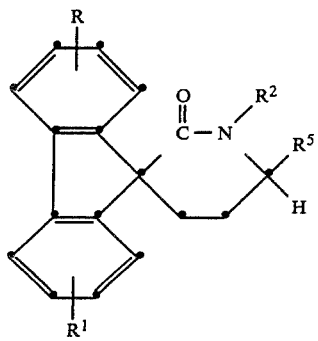

wherein $R^2$ is hydrogen.

15. The compound of claim 14 wherein $R^5$ is hydroxy.

16. The compound of claim 15 wherein R and $R^1$ both are hydrogen.

17. The compound of claim 14 wherein $R^5$ is hydrogen.

18. The compound of claim 17 wherein R and $R^1$ both are hydrogen.

19. A tautomeric mixture of compounds having the formulas

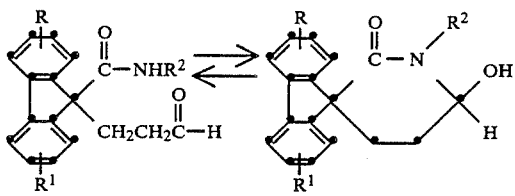

wherein R and $R^1$ independently are hydrogen, $C_1$–$C_4$ alkyl or halo; and $R^2$ is hydrogen or $C_1$–$C_6$ alkyl.

20. The mixture of claim 19 wherein $R^2$ is hydrogen.

21. The mixture of claim 20 wherein R and $R^1$ both are hydrogen.

* * * * *